United States Patent [19]

Busciglio

[11] Patent Number: 4,748,022

[45] Date of Patent: May 31, 1988

[54] TOPICAL COMPOSITION

[76] Inventor: John A. Busciglio, 515 Corner Dr., Brandon, Fla. 33511

[21] Appl. No.: 939,475

[22] Filed: Dec. 9, 1986

Related U.S. Application Data

[63] Continuation of Ser. No. 715,461, Mar. 25, 1985, abandoned.

[51] Int. Cl.$^4$ .................... A61K 35/78; A61K 31/13; A61K 31/075
[52] U.S. Cl. .................... 424/195.1; 514/579; 514/716; 514/717; 514/817; 514/818
[58] Field of Search .................... 424/195.1; 514/579, 514/563, 817, 818, 716, 717

[56] References Cited

U.S. PATENT DOCUMENTS 3,892,853  7/1975  Cobble .......................... 424/195.1

OTHER PUBLICATIONS

Handbook of Nonprescription Drugs, 6th ed 1979, pp. 342 and 419.
B. Havsteen, Biochem. Pharm. vol. 32(7):1141–1148, 1983.

Primary Examiner—J. R. Brown
Assistant Examiner—John W. Rollins, Jr.
Attorney, Agent, or Firm—Frijouf, Rust & Pyle

[57] ABSTRACT

A composition and method of use for the treatment of pain and inflammation associated with lesions of the skin or mucus membrane, such as herpes simplex, herpes labialis, herpes progenitalis, chickenpox lesions, herpes genitalis, sensitivity of gingival tissue due to procedures for etching teeth with HCl, swollen gums, cheilosis, oral traumatic injuries, aphthous ulcer, by applying to the lesion an effective amount of a topical composition comprising diphenhydramine HCl, lidocaine HCl, aloe vera gel, propolis and sufficient base to raise the pH to 8–9.

10 Claims, No Drawings

TOPICAL COMPOSITION

This is a continuation of application Ser. No. 715,461 filed Mar. 25, 1985, now abandoned, the disclosure of which is incorporated herein by reference in its entirety.

BACKGROUND OF THE INVENTION

1. Field of the Invention

The present invention relates to a composition and method of use for the treatment of mucocutaneous lesions by the topical administration of an effective amount of a composition comprising diphenhydramine, lidocaine, aloe, propolis and sufficient base to obtain a pH of 8–9.

2. Description of the Prior Art

Various agents have been used to treat oral lesions within the oral cavity. Among the most widely used are gentian violet, methylene blue, hydrogen peroxide and surfactants, such as ceepyrn (Cepacol). However, these agents have met with limited success and their clinical efficacy leaves much to be desired.

Antihistamines have been commonly employed in dental practice however, mostly for the allergic reactions involving the oral tissues and structures. Among the most widely used antihistamines are ChlorTrimeton, Benadryl, Pyribenzamine and Phenergan. The use of antihistamines has met with very limited success in controlling edema, facial swelling or trismus, etc. resulting from oral surgical procedures.

Corticosteroids have been used in dentistry but only to a limited extent. The most widely used corticosteroid for interoral use is Kenolog (triamcinolone acetonide) which is marketed in an adhesive base (Orabase). The use of this preparation is quite limited since its use is contraindicated in the presence of fungal, viral or bacterial infections of the mouth or throat.

Local anesthetics for topical use are available for dental practice. Tetracaine and dibucaine produce the most adequate topical anesthesia. However, the most widely used is Xylocaine Viscous (lidocaine) available as a 2% aqueous solution adjusted to a pH of 6.0–7.0. It is indicated for use of inflamed and denuded mucus membranes. Generally for an adult an amount of less than 1 ounce, usually ½ ounce, is administered at intervals of not less than 3 hours with no more than 8 doses being administered in a 24 hour period. The maximum single does for a healthy adult is 2 mg/lb body weight and does not in any case exceed a total of 300 mg. The peak effect on the mucus membrane appears in 2–5 minutes and the duration of the effect is 30–60 minutes.

When using oral topical anesthetics the patient is cautioned to avoid food and beverages for one hour after application since the production of topical anesthesia may impair swallowing and thus enhance the danger of aspiration. Numbness of the tongue or buccal mucousal may increase the danger of biting trauma.

Diphenhydramine HCl elixer is used topically as a 10 mg per 4 ml elixir or may be diluted with equal parts of water for its minor anesthetic effect for painful oral conditions such as pemphigus vulgaris, stomatitis, aphthosis and glossodynia. Diphenhydramine is also used topically as a cream (Surfadil) or a lotion (Ziradryl).

Havsteen discusses flavonoids their presence in bee propolis and their therapeutic applications such as pain relief and promotion of healing. B. Havsteen, *Flavanoids, A Class of Natural Products of High Pharmacology Potency,* Biochemical Pharmacology, Volume 32, No. 7, pp. 1141–1148, 1983.

Product literature for a tooth gel "Forever Bright" indicates the use of aloe vera as a inhibitor and a killer of bacteria which are known to cause plaque and bee propolis as having a natural antibiotic action.

U.S. Pat. No. 3,892,853 teaches the use of aloe vera gel by physicians and dentists in relieving pain and in promoting healing of topical and other lesions.

Also in the prior art is a mixture used to treat oral lesions comprising equal amounts of Benadryl, Amphojel and Xylocaine 2% solution, hereinafter Original Composition. The therapeutic dose is one teaspoonful (5 ml) and at low doses this composition does not interfere with swallowing.

The treatment of oral lesions by oral compositions has heretofore met with limited success. With some compositions, the anesthetic effect is coupled with a caution against eating or drinking for about an hour after applying because of the potential aspiration of swallowed material. With other compositions the anesthetic effect either takes too long to reach a therapeutic level or fails to numb the area altogether. For example, the treatment of canker sores which are characterized by ulcers which are confined to the oral mucosa in an otherwise healthy patient, with oral compositions has met with limited success. Present remedies such as spirits of camphor, alcohol 70%, salt water rinses, Blistex, cortizone-like drugs and topical adhering gels such as Orabase have been recommended.

For recurrent or the more troublesome causes of oral lesions such as recurrent herpes simplex or recurrent aphtheloris stomatitis (canker sores) no satisfactory topical treatment is available. The efficacy and safety of neutral red dye and photo therapy (photo inactivation), topical ether or alcohol has not been established. Idoxuridin is of questionable benefit.

A more troublesome oral lesion is secondary to cancer chemotherapy, for example methotrexate therapy. These are large, deep necrotizing ulcers which may effect all mucosal surfaces. Mouth rinses which include a local anesthetic, such as Dyclone, and an antihistamine, such as diphenhydramine, have been used for these lesions.

Zovirox topical ointment is indicated for the treatment of herpes genitalis. Topical application has shown a decrease in healing time and in some cases a decrease in the duration of viral shedding and duration of pain.

What is needed is a composition which will provide relatively longlasting relief of the symptoms associated with oral cavity lesions and promote the healing of the lesions. The composition of the invention allows for the patient to maintain adequate nutritional intake, by relieving symptoms associated with oral lesions.

It is an object of the present invention to provide a mucocutaneous composition that will provide immediate and relatively long-lasting relief from adverse symptoms such as itching, burning and pain caused by mucocutaneous lesions.

It is a further object of the present invention to provide a mucocutaneous composition that will promote healing.

It is a further object of the present invention to provide a mucocutaneous composition which is easy to administer.

It is a further object of the present invention to provide an oral composition that will promote the well being of the patient by diminishing the pain and discomfort of the oral lesion thereby allowing the patient to ingest food and beverages.

It is a further object of the present invention to provide an oral composition which produces a selective topical anesthetic effect at the lesion site(s) when the composition of the invention is applied orally, thereby allowing the ingestion of food and beverages shortly after administration.

The foregoing has outlined some of the more pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description describing the preferred embodiment in addition to the scope of the invention defined by the claims.

SUMMARY OF THE INVENTION

The present invention relates to a composition and method of use for the treatment of pain and inflammation associated with lesions, such as herpes simplex, herpes labialis, herpes progenitalis, chickenpox lesions, herpes genitalis, sensitivity of the gingiva tissue due to procedure for etching teeth with HCl, swollen gums, cheilosis, ulcers resulting from chemotherapy, oral traumatic injury (wound due to puncture from foreign object) and recurrent aphthous stomatitis by administering to the lesion an effective amount of a topical composition comprising diphenhydramine HCl, lidocaine HCl, aloe vera gel, propolis and sufficient base to attain a pH of 8-9. The composition may be applied locally by application with a cotton applicator or orally by swishing throughout the oral cavity, holding for two minutes and expectorating. For treatment of sore throat the patient swishes and gargles the composition throughout the oral cavity, holding for two minutes and then swallowing slowly.

The topical anesthetic onset of action of the composition of the invention is usually about one or two minutes after application with the duration of action usually about twenty to forty minutes.

Both the onset of action and the duration of action by the inventive composition are unexpected since the amount of lidocaine used is less per dose than taught by prior art compositions. Generally in an adult 15 ml (1 tablespoon) of Xylocaine 2% solution is used. This means about 0.3 gram of lidocaine is used per dose verses 0.025 grams per dose, one teaspoonful, of the inventive composition. It is further noted that in the original composition (equal amounts of diphenhydramine elixir, aluminum hydroxide gel and lidocaine viscous (2%)) contains 0.033 grams of lidocaine per dose. Following oral administration of the inventive or original composition the second stage of swallowing (the pharyngeal stage) does not appear to be interfered with thereby permitting the ingestion of food and beverages. This is unexpected since with the majority of oral topical anesthetics the patient is cautioned not to eat or drink within 60 minutes of administering an oral anesthetic throughout the oral cavity to prevent the possible aspiration of food. Surprisingly, the numbness produced by the composition of the invention appears to be selective i.e., mostly at the lesion site. This is based on the fact that a patient using the inventive composition experiences diminished adverse symptoms, but is still able to taste food and beverages.

Hence, inventive composition not only facilitates eating, but also provides short-term pain relief (numbness) which allows for the ingestion of oral therapeutic drugs such as maintenance drugs or antipyretic drugs, if needed.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other compositions for carrying out the same purposes of the present invention. It should also be realized by those skilled in the art that such equivalent constructions do not depart from the spirit and scope of the invention as set forth in the appended claims.

DETAILED DESCRIPTION OF THE INVENTION

The composition of the instant invention promotes healing and relieves adverse symptoms such as burning and pain, associated with irritated–inflammed mucous membrane of the mouth and throat. The composition of the invention is composed of five elements:
diphenhydramine HCl about : 0.06% to 0.09% by weight
lidocaine HCl about: 0.5% to 0.7% by weight
aloe vera gel about: 20% to 35% by weight
propolis about: 1% to 2% by weight and sufficient base to raise the pH to 8-9, plus any necessary pharmaceutical excipients.

The frequency of the dose is at least 3 or 4 times per day and the dose quantity is one teaspoonful (5 ml.). The maximum dosage is about 2.4 grams (lidocaine HCl) per 24 hours in equally divided intervals.

The base is selected from the group consisting of aluminum hydroxide gel, magnesium hydroxide mixture such as Maalox. It is critical to the invention that the pH of the final solution be within a range of 8-9. That is, while any base which is pharmaceutically acceptable may be used in the invention to attain the desired pH, it is critical that the pH be in the range of 8-9. The aforementioned bases appear to prepare the most pharmaceutically elegant composition.

Aloe vera gel relieves pain and promotes healing of topical lesions. The stabilized form provides the longest shelf life and therapeutic efficacy without refrigeration. The aloe vera gel used in the inventive composition should be pure. Aloe vera gel is readily available as see U.S. Pat. No. 3,892,853. There are many aloe vera gel preparations available. For the inventive composition, the amount of aloe vera gel is based on the more pure forms, namely about 99-100% pure. Lidocaine HCl and diphenhydramine HCl may be added either as the aqueous solution (2% Xylocaine Viscous) or the elixir (Benadryl Elixir) respectively or as any form available to attain the required amount.

The therapeutic applications of bee propolis are reported to be the promotion of healing, relief of pain, antibiotic action, among others. These actions are based on the presence of flavonoids in the propolis.

The composition is a liquid for ease of administration throughout the oral cavity or mucous membrane.

Pharmaceutical preservatives, such as methylparaben and propylparaben, may be used. The only criteria in the selection of a preservative is that it would not be incompatible with the active ingredients. Flavorants, such as cinnamon, peppermint and spearmint may be used. Thickening agents such as sodium carboxymethylcellulose, carrogeen may also be used. Sweetening agents such as Nutra-Sweet, sugar, or sodium saccharin may also be used.

The selection of any or all of the above pharmaceutical excipients can be made by one skilled in the art of pharmaceutical preparations. Moreover, the active ingredients may also be delivered to the lesion site by way of a cream base. However, the pH of the resultant cream must be 8-9.

EXAMPLE

In order to prepare 120 ml (liquid) of the composition of the invention:
Amphojel (aluminum hydroxide gel): 30 ml
Benadryl (diphenhydramine HCl 10 mg/4 ml) elixir: 30 ml (75.0 mg)
2% Xylocaine viscous: 30 ml (0.6 gm)
Aloe (100% pure): 30 ml
Three, 500 mg propolis tablets: 1.5 grams (1.25% w/v)

Crush the tablets in a mortar and pestal, add other ingredients to attain a volume of 120 ml and mix well to insure proper dispersion of the ingredients. Flavorants, sweeteners and other pharmaceutical excipients may be added, however, the pH of the final product must be in the range of 8-9.

The composition of the invention is applied to mucocutaneous lesions at least 3 or 4 times per day. For application to the skin, a sufficient amount is applied to the lesion site which relieves the adverse symptoms. The maximum dosage is the amount of the inventive composition which contains about 2.4 grams lidocaine per 24 hours applied in equally divided intervals.

COMPARATIVE DATA

In order to compare the effect of the added aloe and propolis in relieving burning and pain and in the promotion of healing, three composition were prepared. Composition no. 1 (prior art) was composed of three equal amounts of Benadryl elixir, Xylocaine viscous 2% and Amphojel. Composition no. 2 (composition of the inventio) was composed of equal amounts of Benadryl elixir, Xylocaine viscous 2%, Amphojel, aloe vera gel and 1.5 grams of propolis per 120 ml of composition. Composition no. 3 (not prior art—comparative composition) was composed of equal amounts of Benadryl elixir, Xylocaine viscous 2%, Amphojel and aloe vera gel (100% pure).

Various lesions were treated:
(1) Aphthous ulcer
(2) Sensitivity of gingival tissue due to etching of teeth procedure using HCl etchant
(3) Traumatic injury (wound due to puncture from foreign object)
(4) Swollen gums
(5) Cheilosis (cracks in corner of mouth)
(6) Herpes simplex (canker sore, fever blister)

The mixtures were applied either locally to the lesion itself, that is, by way of a cotton applicator where the composition remained in contact with the lesion for two minutes or they were applied orally (entire oral cavity treated) to the lesion, that is, the mixture was taken into the mouth, swished around the oral cavity without gargling, held for two minutes and then expectorated. The entire oral cavity was treated unless noted otherwise. The patient tested in each group was about 14 years of age with the youngest and oldest for all groups being 8 years and 36 years respectively. The dose was one teaspoonful (5 ml) given 3 or 4 times per day.

Of those treating their oral lesions with composition no. 1, they respond as to the effectiveness:
very effective: 1
effective: 4
not effective: 1
The lesions treated were:
very effective: traumatic injury (1)*
effective: traumatic injury (2); aphthous ulcer (1); gingival sensitivity to etch compound (1)
non effective: cheilosis (1)
*Refers to number of patients responding to a particular lesion.

Of those treating their oral lesion with composition no. 2, they responded as to the effectiveness:
very effective: 8
effective: 8
not effective: none
The lesions treated were:
very effective: aphthous ulcer (1); gingival sensitivity due to etch compound (2); traumatic injury (2); swollen gums (1); herpes simplex (2) (one patient applied the composition to the lesion with a cotton applicator)
effective: aphthous ulcer (3) (one patient applied the composition to the lesion with a cotton applicator); traumatic injury (4); cheilosis (1)

Of those treating their oral lesion with composition no. 3, they responded as to the effectiveness:
very effective: 3
effective: none
not effective: none
The lesions treated were: aphthous ulcer (2); traumatic injury (1)

Days to heal:
It is noted that with or without the use of a topical agent, healing usually occurs itself, for example with canker sores within ten days.

Composition no. 1 took the longest time averaging 7.1 days.

Composition no. 2 averaged 4.8 days and composition no. 3 averaged 3 days; however, one patient stated that the composition did not heal at all.

All of the users of the composition no. 2 expressed that the composition "brought comfort". The majority of users of mixtures no. 1 and 3 expressed that it also brought comfort, however some noted that it only brought "some comfort".

The above data represents a surprising and unexpected result since the prior art teaches using stronger concentration of lidocaine to attain a similar therapeutic response. Not only is the effective dose lower, but the therapeutic response as measured by the comfort after use is better in the inventive composition.

A lower effective dose with the same frequency means less chance of toxic or adverse actions. Furthermore, the chance for the development of hypersensitivity due to repeated applications of lidocaine to the mucous membrane may be lessened.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed:

1. A composition for the treatment of pain and inflammation associated with lesions of skin or mucous membrane comprising:
   lidocaine HCl: about 0.5 to 0.7 percent by weight;
   diphenhydramine HCl: about 0.06 to 0.09 percent by weight;
   aloe vera gel (100% pure): about 20 to 35 percent by weight;
   propolis 1-2 percent by weight and sufficient base to raise the pH of the final composition to 8-9 plus a suitable pharmaceutical excipient(s).

2. The composition of claim 1 wherein the pharmaceutical excipient is a flavoring agent.

3. The composition of claim 1 wherein the pharmaceutical excipient is a preservative.

4. The composition of claim 1 wherein the pharmaceutical excipient is a sweetening agent.

5. The composition of claim 1 wherein the base is aluminum hydroxide gel.

6. A method for the treatment of pain and inflammation associated with lesions of the skin or mucous membrane comprising applying to the lesion an effective amount of a composition comprising:
   lidocaine HCl: about 0.5 to 0.7 percent by weight;
   diphenhydramine HCl: about 0.06 to 0.09 percent by weight;
   aloe vera gel (about 99-100% pure): about 20 to 35 percent by weight;
   propolis: about 1-2 percent by weight;
   and sufficient base to raise the pH of the final composition to 8-9, plus a suitable pharmaceutical excipient(s).

7. The method of claim 6 for the treatment of pain and inflammation associated with oral lesions of the mucous membrane comprising applying to the oral lesion an effective amount of a composition comprising:
   lidocaine HCl: about 0.5 to 0.7 percent by weight;
   diphenhydramine HCl: about 0.06 to 0.09 percent by weight;
   aloe vera gel (about 99-100% pure): about 20 to 35 percent by weight;
   propolis: about 1-2 percent by weight;
   and sufficient base to raise the pH of the final composition to 8-9, plus a suitable pharmaceutical excipient(s).

8. The method of claim 7 wherein the composition is applied to lesions in the oral cavity by taking an effective amount of the composition into the mouth, swishing around the oral cavity, holding for about two minutes and then expectorating.

9. The method of claim 6 wherein an effective amount of the composition is topically applied to lesions of the skin associated with chickenpox.

10. The method of claim 6 wherein an effective amount of the composition is typically applied to lesions of the skin associated with herpes genitalis.

* * * * *

UNITED STATES PATENT AND TRADEMARK OFFICE
CERTIFICATE OF CORRECTION

PATENT NO. : 4,748,022
DATED : May 31, 1988
INVENTOR(S) : John A. Busciglio

It is certified that error appears in the above-identified patent and that said Letters Patent are hereby corrected as shown below:

In the Specification

Col. 4, line 44, after "hydroxide" 2nd occurrence insert --(milk of magnesia) or an aluminum hydroxide magnesium hydroxide--.

Signed and Sealed this

First Day of November, 1988

Attest:

DONALD J. QUIGG

Attesting Officer

Commissioner of Patents and Trademarks